US009474451B2

(12) United States Patent
Brady et al.

(10) Patent No.: US 9,474,451 B2
(45) Date of Patent: Oct. 25, 2016

(54) SYSTEMS AND METHODS FOR VARYING BLOOD FLOW TO IDENTIFY AUTOREGULATORY RANGES IN A PATIENT

(75) Inventors: Ken M. Brady, Sugar Land, TX (US); Robert A. Baruch, Ellicott City, MD (US)

(73) Assignee: Raba Equity Partners II, LLC, Ellicott City, MD (US)

( * ) Notice: Subject to any disclaimer, the term of this patent is extended or adjusted under 35 U.S.C. 154(b) by 757 days.

(21) Appl. No.: 13/433,348

(22) Filed: Mar. 29, 2012

(65) Prior Publication Data
US 2012/0253211 A1 Oct. 4, 2012

Related U.S. Application Data

(60) Provisional application No. 61/470,601, filed on Apr. 1, 2011.

(51) Int. Cl.
*A61B 5/02* (2006.01)
*A61B 5/03* (2006.01)
(Continued)

(52) U.S. Cl.
CPC ........... *A61B 5/02028* (2013.01); *A61B 5/031* (2013.01); *A61B 5/14553* (2013.01); *A61M 1/1086* (2013.01); *A61B 5/021* (2013.01); *A61B 5/026* (2013.01); *A61M 1/3666* (2013.01)

(58) Field of Classification Search
CPC ........... A61B 5/0002; A61B 5/02007; A61B 5/0205; A61B 5/021; A61B 5/02141; A61B 5/022; A61B 5/024; A61B 5/02438; A61B 5/026; A61B 5/0261; A61B 5/0265; A61B 5/027; A61B 5/028; A61B 5/029; A61B 5/0535; A61B 5/1073; A61B 5/222; A61B 5/681; A61B 5/6855; A61B 5/6856; A61B 5/7257; A61B 8/06; A61B 5/031; G06F 19/322; G06F 19/3406; G06F 19/3418; G06Q 50/22; A61M 1/3666
USPC ........ 600/300, 301, 481, 483, 504, 505, 507
See application file for complete search history.

(56) References Cited

U.S. PATENT DOCUMENTS 4,557,270 A * 12/1985 John ............................. 600/544
6,328,698 B1 12/2001 Matsumoto
(Continued)

FOREIGN PATENT DOCUMENTS

WO WO 2009/058353 A1 5/2009
WO WO 2010/084347 A1 7/2010

OTHER PUBLICATIONS

International Search Report and Written Opinion dated Nov. 1, 2012 issued in corresponding PCT application No. PCT/US2012/031363, 9 pages.
(Continued)

*Primary Examiner* — Jacqueline Cheng
*Assistant Examiner* — Puya Agahi
(74) *Attorney, Agent, or Firm* — Snyder, Clark, Lesch & Chung, LLP

(57) ABSTRACT

A method may include controlling a bypass pump to introduce blood flow variations to a patient. The method may also include analyzing blood volume in the brain of the patient with respect to the blood flow variations and determining, based on the analyzing, whether an autoregulatory mechanism associated with the brain is operating properly.

20 Claims, 9 Drawing Sheets

(51) Int. Cl.
*A61B 5/1455* (2006.01)
*A61M 1/10* (2006.01)
*A61B 5/021* (2006.01)
*A61B 5/026* (2006.01)
*A61M 1/36* (2006.01)

(56) References Cited

U.S. PATENT DOCUMENTS

| | | | |
|---|---|---|---|
| 6,447,441 B1 | 9/2002 | Yu et al. | |
| 6,475,186 B1* | 11/2002 | Safar et al. | 604/101.05 |
| 6,692,443 B2* | 2/2004 | Crutchfield et al. | 600/504 |
| 6,785,568 B2* | 8/2004 | Chance | 600/340 |
| 6,802,812 B1* | 10/2004 | Walker et al. | 600/309 |
| 6,949,080 B2* | 9/2005 | Wolf et al. | 604/8 |
| 8,157,760 B2* | 4/2012 | Criado et al. | 604/9 |
| 2002/0091320 A1* | 7/2002 | Crutchfield et al. | 600/454 |
| 2003/0158471 A1* | 8/2003 | Narimatsu et al. | 600/321 |
| 2004/0068220 A1 | 4/2004 | Couvillon, Jr. et al. | |
| 2004/0147869 A1* | 7/2004 | Wolf et al. | 604/8 |
| 2006/0094964 A1* | 5/2006 | Ragauskas et al. | 600/454 |
| 2006/0122554 A1* | 6/2006 | Wilk | 604/8 |
| 2006/0184051 A1* | 8/2006 | Hempstead et al. | 600/485 |
| 2007/0287922 A1* | 12/2007 | Tanaka et al. | 600/485 |
| 2008/0281178 A1* | 11/2008 | Chuang et al. | 600/347 |
| 2009/0024072 A1* | 1/2009 | Criado et al. | 604/9 |
| 2009/0156945 A1* | 6/2009 | Baruch | 600/484 |
| 2009/0177279 A1* | 7/2009 | Luciano et al. | 623/11.11 |
| 2009/0227881 A1* | 9/2009 | Reichman et al. | 600/506 |
| 2009/0270734 A1* | 10/2009 | Ragauskas | A61B 5/026 600/454 |
| 2010/0010322 A1* | 1/2010 | Brady | 600/301 |
| 2010/0030054 A1* | 2/2010 | Baruch et al. | 600/368 |
| 2010/0049082 A1* | 2/2010 | Hu et al. | 600/561 |
| 2010/0054975 A1* | 3/2010 | Ibragimov | 417/477.3 |
| 2010/0063405 A1* | 3/2010 | Kashif et al. | 600/485 |
| 2010/0241047 A1 | 9/2010 | Yacoubian et al. | |
| 2010/0331684 A1* | 12/2010 | Ragauskas et al. | 600/438 |
| 2011/0105912 A1* | 5/2011 | Widman | A61B 5/02028 600/483 |
| 2011/0172545 A1* | 7/2011 | Grudic et al. | 600/485 |
| 2012/0130697 A1* | 5/2012 | Woodford | 703/11 |

OTHER PUBLICATIONS

Brady, K.M., Shaffner, D.H., Lee, J.K., Easley, R.B., Smielewski, P., Czosnyka, M., Jallo, G.I., and Guerguerian, A.M. (2009), Continuous monitoring of cerebrovascular pressure reactivity after traumatic brain injury in children. *Pediatrics* 124, e1205-1212.
Steiner, L.A., Czosnyka, M., Piechnik, S.K., Smielewski, P., Chatfield, D., Menon, D.K., and Pickard, J.D. (2002), Continuous monitoring of cerebrovascular pressure reactivity allows determination of optimal cerebral perfusion pressure in patients with traumatic brain injury. *Critical care medicine* 30, 733-738.
Brady, K.M., Mytar, J.O., Lee, J.K., Cameron, D.E., Vricella, L.A., Thompson, W.R., Hogue, C.W., and Easley, R.B. (2010), Monitoring cerebral blood flow pressure autoregulation in pediatric patients during cardiac surgery. *Stroke*; 41, 1957-1962.
Brady, K.M., Lee, J.K., Kibler, K.K., Smielewski, P., Czosnyka, M., Easley, R.B., Koehler, R.C., and Shaffner, D.H. (2007), Continuous time-domain analysis of cerebrovascular autoregulation using near-infrared spectroscopy. *Stroke*; 38, 2818-2825.
Brady, K.M., Lee, J.K., Kibler, K.K., Easley, R.B., Koehler, R.C., and Shaffner, D.H. (2008), Continuous measurement of autoregulation by spontaneous fluctuations in cerebral perfusion pressure: Comparison of 3 methods. *Stroke* 39, 2531-2537.
Brady, K., Joshi, B., Zweifel, C., Smielewski, P., Czosnyka, M., Easley, R.B., and Hogue, C.W., Jr. (2010), Real-time continuous monitoring of cerebral blood flow autoregulation using near-infrared spectroscopy in patients undergoing cardiopulmonary bypass. *Stroke*; 41, 1951-1956.
Joshi, B., Brady, K., Lee, J., Easley, B., Panigrahi, R., Smielewski, P., Czosnyka, M., and Hogue, C.W., Jr. (2010), Impaired autoregulation of cerebral blood flow during rewarming from hypothermic cardiopulmonary bypass and its potential association with stroke. *Anesthesia and Analgesia* 110, 321-328.
Czosnyka, M., Brady, K., Reinhard, M., Smielewski, P., and Steiner, L.A. (2009), Monitoring of cerebrovascular autoregulation: Facts, myths, and missing links. *Neurocritical care*; 10, 373-386.
Czosnyka, M., Smielewski, P., Kirkpatrick, P., Menon, D.K., and Pickard, J.D. (1996), Monitoring of cerebral autoregulation in head-injured patients. *Stroke*; 27, 1829-1834.
Czosnyka, M., Smielewski, P., Kirkpatrick, P., Laing, R.J., Menon, D., and Pickard, J.D. (1997), Continuous assessment of the cerebral vasomotor reactivity in head injury. *Neurosurgery* 41, 11-19.
Lee, J.K., Kibler, K.K., Benni, P.B., Easley, R.B., Czosnyka, M., Smielewski, P., Koehler, R.C., Shaffner, D.H., and Brady, K.M. (2009), Cerebrovascular reactivity measured by near-infrared spectroscopy. *Stroke* 40, 1820-1826.
Ragauskas, A., Daubaris, G., Petkus, V., Ragaisis, V., and Ursino, M. (2005), Clinical study of continuous non-invasive cerebrovascular autoregulation monitoring in neurosurgical icu. *Acta neurochirurgica.Supplement* 95, 367-370 (abstract only).

* cited by examiner

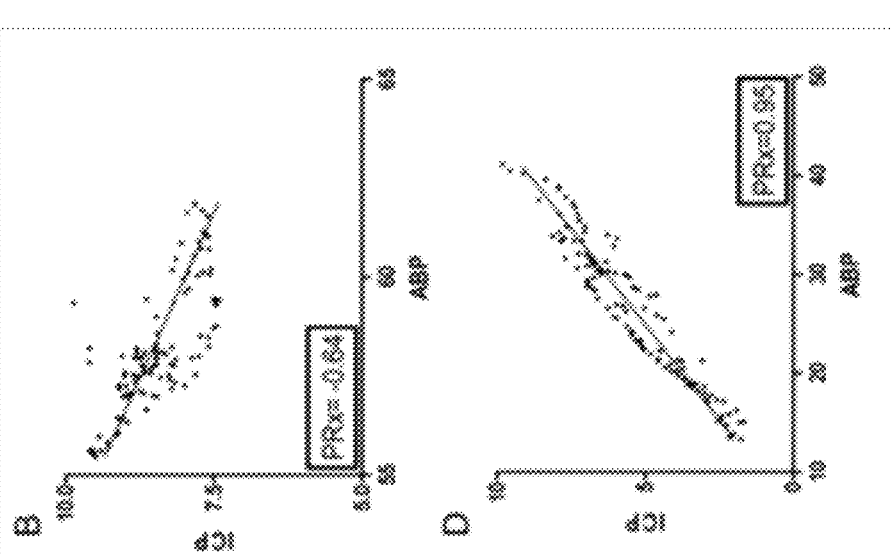
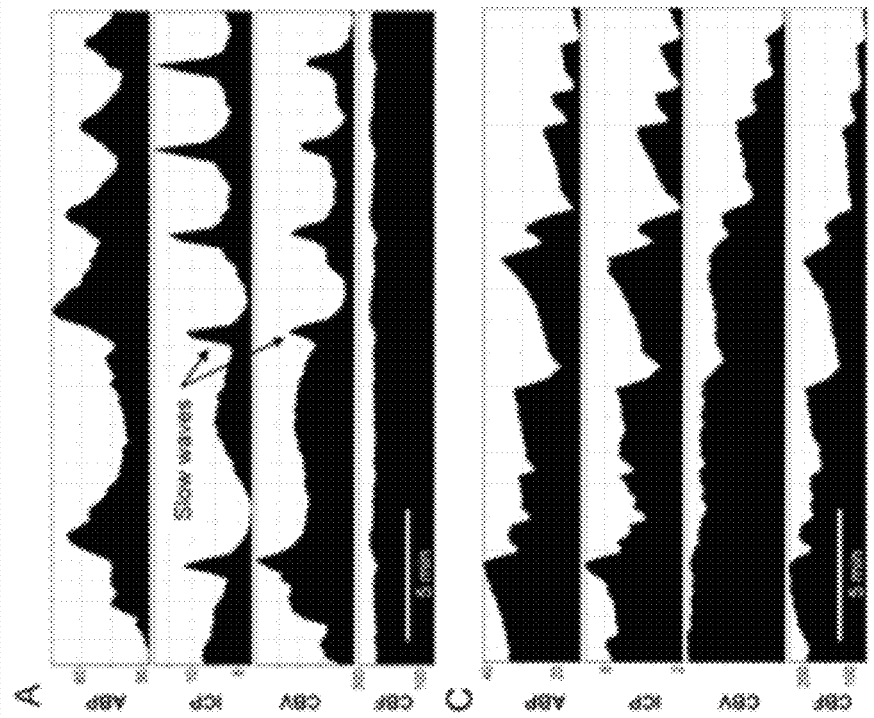

US 9,474,451 B2

SYSTEMS AND METHODS FOR VARYING BLOOD FLOW TO IDENTIFY AUTOREGULATORY RANGES IN A PATIENT

RELATED APPLICATION

This application claims priority under 35 U.S.C. §119 based on U.S. Provisional Patent Application No. 61/470,601, filed Apr. 1, 2011, the disclosure of which is hereby incorporated herein by reference.

BACKGROUND INFORMATION

Neurologic injury occurs in approximately 30-70% of children who require cardiac surgery. While the brain is considered "the heart of the matter" by the congenital cardiac surgery team, critical details of care during cardiopulmonary bypass (CPB) vary between cardiac surgery centers. Neurologic injury from CPB requires a multifaceted solution, including improved real-time assessment of the adequacy of cerebral blood flow.

For example, autoregulation refers to the maintenance of constant cerebral blood flow across a range of cerebral perfusion pressures. Autoregulation is a homeostatic mechanism that protects the brain from excessive or inadequate blood flow. Monitoring autoregulation may be useful during cardiopulmonary bypass. Patients with impaired autoregulation are more likely to die or suffer permanent neurologic disability. Autoregulation monitoring can be used to delineate care practices that enhance the ability of the brain to regulate its own blood flow. However, conventional autoregulation monitoring often takes a considerable amount of time.

BRIEF DESCRIPTION OF THE DRAWINGS

FIGS. 1A-5 illustrate experimental data associated with conventional methods for assessing cerebral vascular reactivity;

DETAILED DESCRIPTION OF PREFERRED EMBODIMENTS

Figure 2:
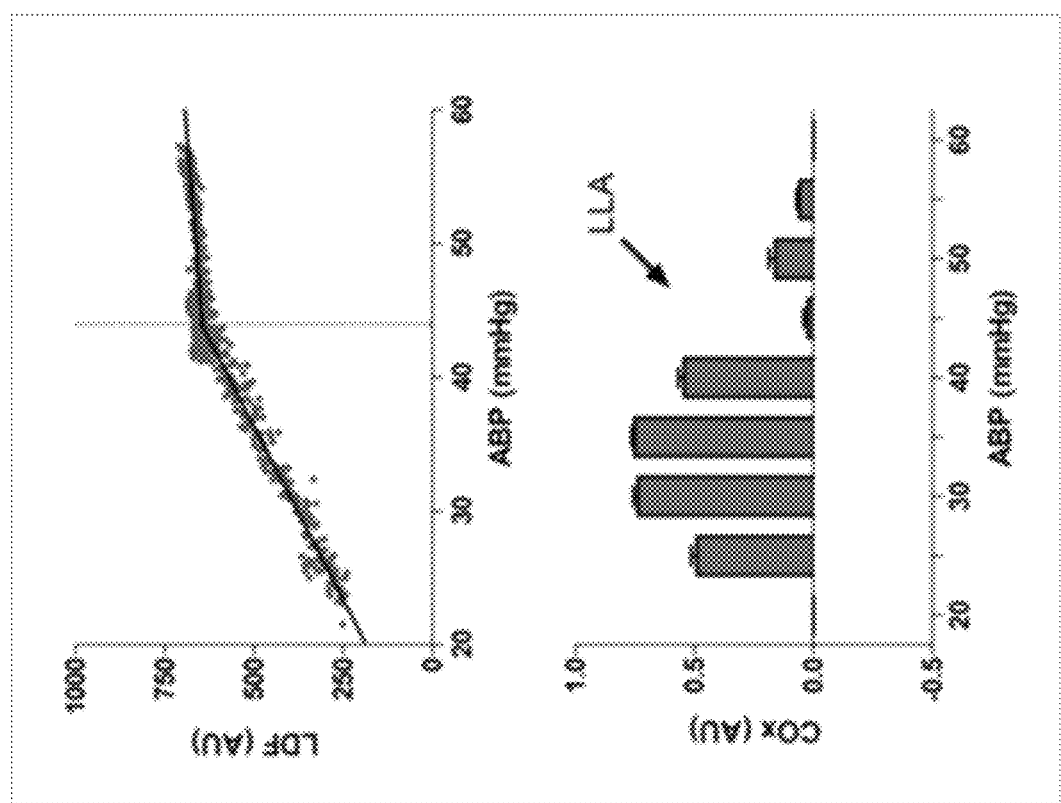

The following detailed description refers to the accompanying drawings. The same reference numbers in different drawings may identify the same or similar elements. Also, the following detailed description does not limit the invention. Instead, the scope of the invention is defined by the appended claims and their equivalents.

Implementations described herein provide methods, systems and computer program products for monitoring cerebrovascular autoregulation to optimize hemodynamic management for patients. In one implementation, repetitive, hemodynamic oscillations (referred to as "slow waves") are induced by varying blood flow to a patient via a cardiopulmonary bypass (CPB) pump/system. These induced "slow waves" allow for precise measurements with respect to autoregulation in a very short period of time. The measurements may also allow medical personnel to quickly ascertain certain conditions and optimize care for a patient.

Two non-invasive metrics of autoregulation using near-infrared spectroscopy have been developed. However, barriers to translation of this technology, especially the sporadic and variable nature of pressure waves required for a monitoring signal during CPB have been identified. In implementations described herein, flow variations of fixed amplitude and period in an otherwise silent bandwidth between respiratory and slow wave frequencies are introduced into the patient using CPB pumps/systems. Within this bandwidth, a family of metrics of autoregulation may be generated. These metrics include features designed for precision, and the ability to delineate optimal CPB flow to the patient.

In particular, embodiments described herein analyze the relationship between an input waveform that is derived from pump flow oscillation of a CPB pump and the end-organ "response" waveform that is affected by the organ vascular response. Examples of the input waveform may include: arterial blood pressure, post-roller head pressure, the pump flow rate, or another variable with a relationship to the pump flow input. Examples of the response waveform include intracranial pressure, fontanel pressure, blood flow velocity, end-organ oxyhemoglobin saturation, end-organ hemoglobin density, or other metrics of organ blood volume, flow, or oxygenation. Examples of relationship quantification between the input and response waveforms include phase angle, correlation, coherence, gain of transfer, or other analysis of waveform quality. Because the input wave (i.e., slow wave) is determined or engineered to provide a consistent, repeatable waveform, the input waveform can be optimized to be the fastest waveform that evokes an autoregulatory response in the organ of interest.

Still further, implementations described herein allow a user to program a family of autoregulation metrics using pump oscillations that are determined from measurements associated with transition bandwidth measurements that identify weak and robust autoregulation limits. In such implementations, the inputs are pump oscillations, blood pressure, and circuit pressure, and outputs are cortical red cell flux, cerebral blood volume, and cerebral oximetry. Functions include correlation, gain of transfer, and phase analysis.

In addition, in some implementations, the precision and accuracy of the family of autoregulation metrics discussed above may be quantified. Such measurements may provide a determination of the lower limit of autoregulation (LLA).

In summary, in implementations described herein, a new family of autoregulation metrics may be generated, which can then be applied to autoregulation during CPB, as well as the general field of cerebrovascular monitoring and CPB practices.

As described above, neurologic injury occurs in approximately 30-70% of children with congenital heart disease (CHD) during surgical repair. The recent use of magnetic resonance imaging (MRI) pre- and post-operatively in this population has uncovered this high incidence of brain injury acquired during surgery. As a result, this population demands meticulous hemodynamic support during surgery and CPB.

High-flow rates, afterload reduction, ultrafiltration techniques, and selective cerebral perfusion strategies have been used over the last two decades, which have seen a tremendous improvement in survival from previously fatal cardiac lesions. However, perfusion of the brain is not dependent on cardiac output or pump flow rates. For example, the brain is a uniquely pressure-dependent organ. Without defining the limits of autoregulation, it is not possible to safely titrate afterload reduction when indicated for cardiac surgical patients.

In prior systems, a method to measure autoregulation as a continuously monitored parameter using arterial pressure and near-infrared spectroscopy was developed. Such a method was shown to identify a lower limit of autoregulation in a large percentage of pediatric patients during cardiopulmonary bypass. The lower limits of autoregulation identified in this cohort ranged from 25 to 55 millimeters (mm) of mercury (Hg). In a cohort of adult patients with the same monitoring, the lower limit of autoregulation was found to range from 45 to 80 mm Hg. In the adult cohort, impaired autoregulation during rewarming was found to be associated with stroke.

In general, conventional methods to monitor autoregulation suffer from imprecision caused by the sporadic nature of spontaneous low frequency waves (e.g., slow waves) of arterial blood pressure required for the analysis. Reliance on slow wave activity creates long time requirements for delineating the boundaries of autoregulation in the clinical setting. The infrared technique, which is well-suited to patients on bypass, has a drawback when applied to children. For example, cyanotic heart disease confounds the assumption that cerebral oximetry waveforms recapitulate slow-wave activity. This is because arterial oxygen fluctuations occur in the same range of frequencies or bandwidth as slow wave activity, rendering the pre-bypass recordings useless for determination of the lower limit of autoregulation.

Children with the greatest risk of neurologic injury during CPB often require repair of the aortic arch that requires selective cerebral perfusion, a clinical scenario that lacks accessible blood pressure measurements required for autoregulation analysis. In accordance with one implementation described herein, an input signal using oscillations of the CPB pump with a magnitude approximately equal to respiratory variation, but is slower, and tailored to the actual clinical scenario, is introduced to the patient. Signals from these waves may give faster, more precise and more accurate information than the signals obtained from spontaneous slow waves used in previous methods, as described in more detail below.

Further, the methodologies described herein can be used without arterial blood pressure monitoring, which opens the possibility of optimizing flow rates while applying selective cerebral perfusion techniques.

One conventional continuous autoregulation monitoring method uses the mean velocity index, a moving linear correlation coefficient between cerebral perfusion pressure and middle cerebral artery flow velocity. Many other conventional techniques generally dichotomize between indices of autoregulation proper (using cerebral blood flow surrogates to gauge constraint of flow) and indices of vascular reactivity (using cerebral blood volume surrogates to gauge reactivity of resistance vessels).

For example, FIGS. 1A-1D depict the rationale behind these metrics with the pressure reactivity index (PRx), which uses intracranial pressure (ICP) as a surrogate of cerebral blood volume. The PRx can define optimal perfusion pressures in adults with traumatic brain injury, and deviation from this pressure is associated with death and persistent vegetative state. Regardless of the modality used to measure autoregulation, it is necessary to have a change in arterial blood pressure to examine the autoregulatory reaction. When autoregulation is intact, changes in pressure cause vascular reactivity, as shown in FIG. 1A, with accompanying example of pressure reactivity (PRx) calculation by simple correlation of arterial blood pressure and intracranial pressure, as illustrated in FIG. 1B.

When autoregulation is intact, cerebral blood volume changes in opposition to changes in arterial blood pressure, hence it is termed reactive, and gives a negative correlation. In the frequency domain, this would result in a large phase angle difference between the two waves. FIGS. 1C and 1D show the result of failed autoregulation, when the cerebral vasculature is passive to changes in arterial blood pressure. In the passive state, cerebral blood volume and flow changes are in phase with arterial blood pressure changes, and this yields a positive linear correlation between them.

In addition, non-invasive metrics of autoregulation with reflectance near-infrared spectroscopy have been developed. The first was the cerebral oximetry index (COx), a linear correlation between cerebral oximetry and arterial blood pressure. It has been shown that the COx detects the lower limit of autoregulation in piglet models, as illustrated in FIG. 2. For example, referring to FIG. 2, when the piglet has a blood pressure less than 40 mm Hg, the blood flow to the brain is pressure passive (shown in the top graph), and this is detected by a jump in the cerebral oximetry index, describing passivity of cerebral oximetry to blood pressure (shown at the bottom graph). With such a display at the bedside, it is evident that the piglet requires a blood pressure greater than 40 millimeters (mm) of mercury (Hg) to maintain intact cerebrovascular responses. As a result, this methodology can be used to obtain an LLA.

Figure 3:
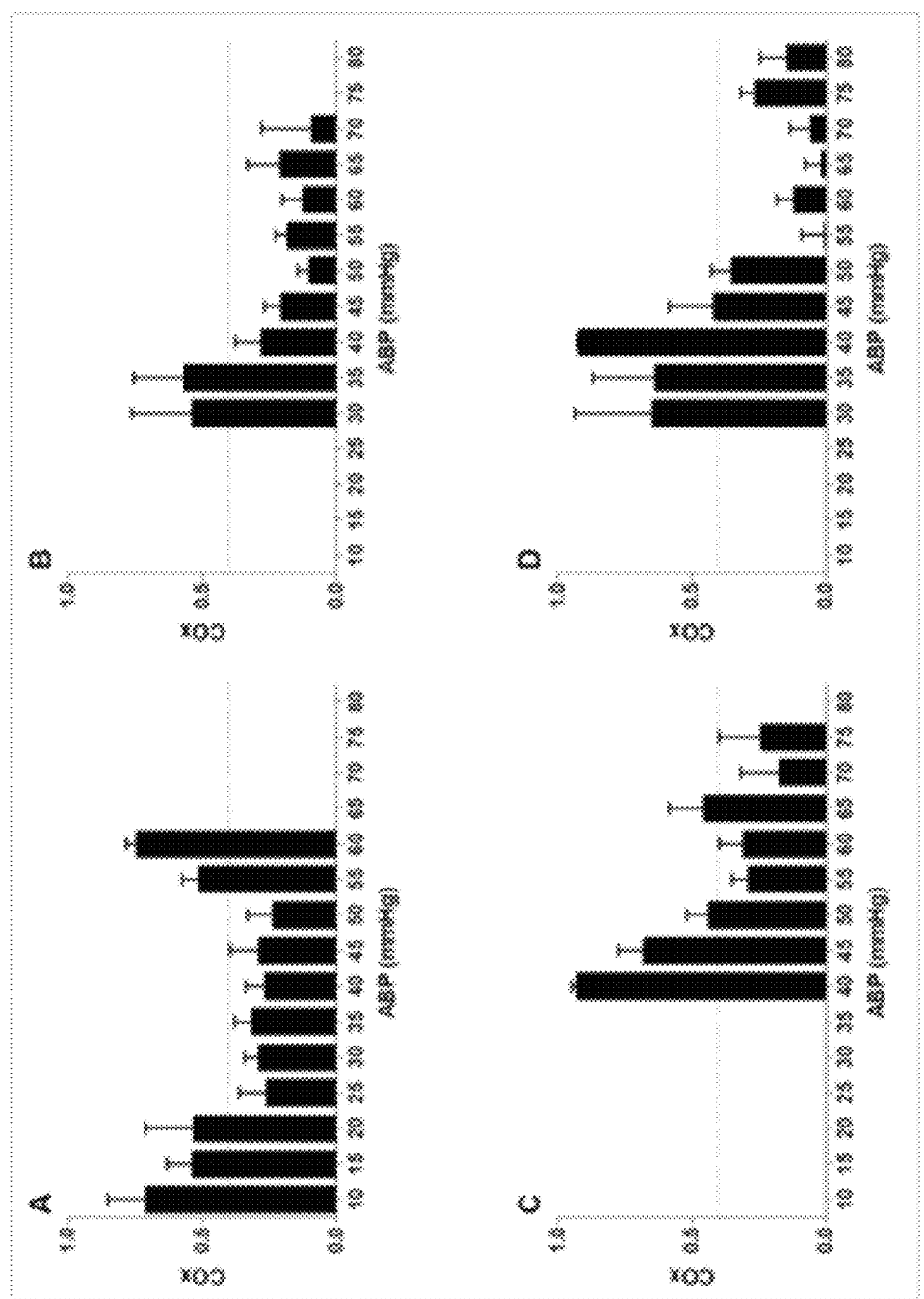

The cerebral oximetry methodology also includes recording the cerebral oximetry index in both pediatric and adult patients during cardiac surgery (in real time) to delineate the LLA for patients undergoing cardiopulmonary bypass, as illustrated in FIG. 3. For example, referring to FIG. 3, the individual autoregulation curves in children with COx monitoring during CPB identifies the LLA. For example, the infant shown in graph A is fine with arterial blood pressure (ABP) in the 30's, but not so for the other patients in graphs B, C and D of FIG. 3, where COx values are greater than 0.45 (shown via the dotted line), which suggests autoregulation impairment.

Figure 4:
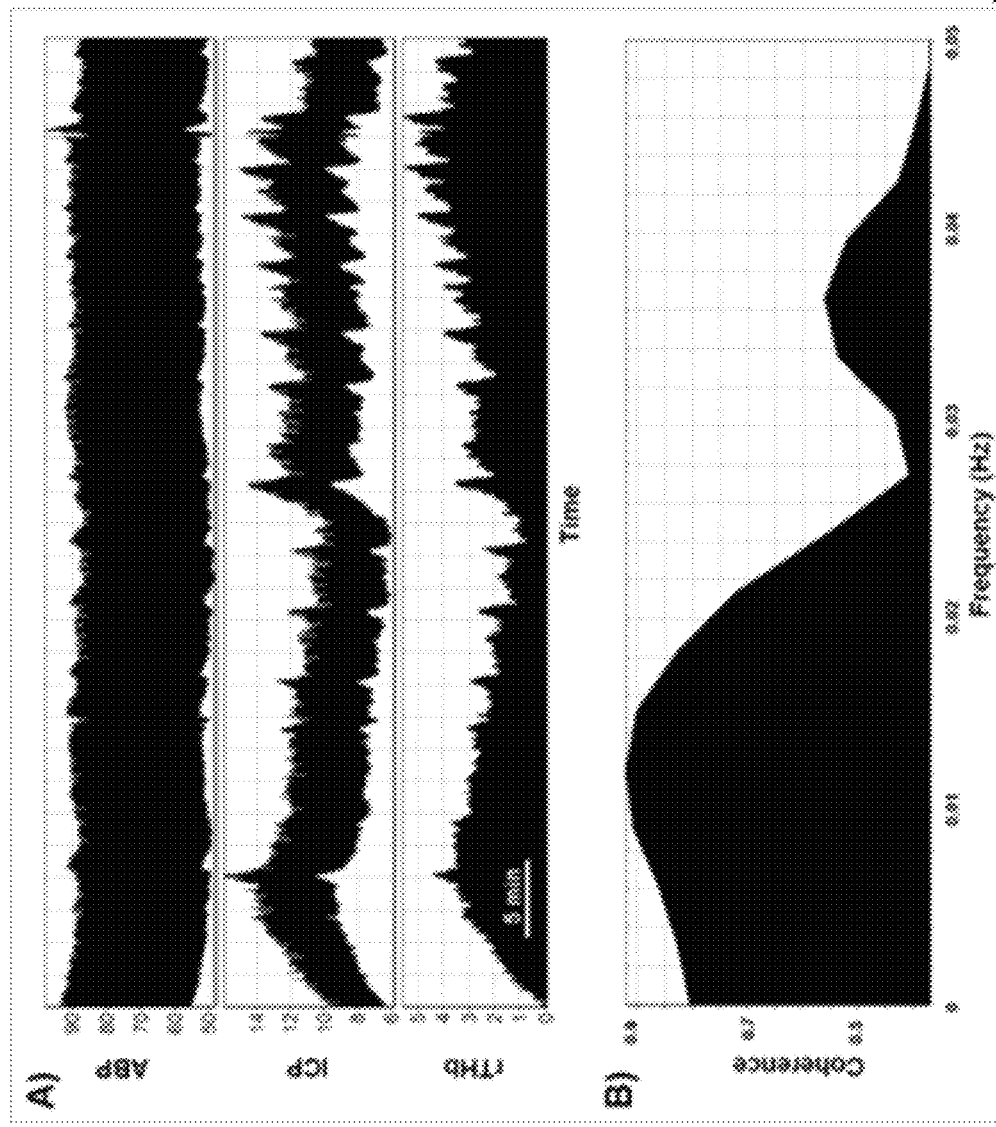

It has been shown that blood volume estimated in this way trends intracranial pressure, as illustrated in FIG. 4. Referring to the top graph in FIG. 4 (labeled A), ABP, intracranial pressure (ICP) and relative total hemoglobin (rTHb) measured with infrared spectroscopy are shown. In graph B of FIG. 4, coherence between ICP and rTHb is high at the slow wave frequency. However, generating the PRx takes a considerable amount of time and may not be used for patients undergoing selective cerebral perfusion that often do not have accurate arterial pressure monitoring.

In accordance with an exemplary implementation described herein, slow waves are introduced into the pump during CPB. In one implementation, the slow waves may be engineered to be continuous, consistent, and at a frequency that minimizes the time to deliver critical data. These waves are selected and engineered to be faster than naturally occurring slow waves, where autoregulatory responses to blood pressure changes are complete, but slower than respiratory waves, where autoregulatory responses to blood pressure changes are partial, as illustrated in FIG. 5.

Figure 5:
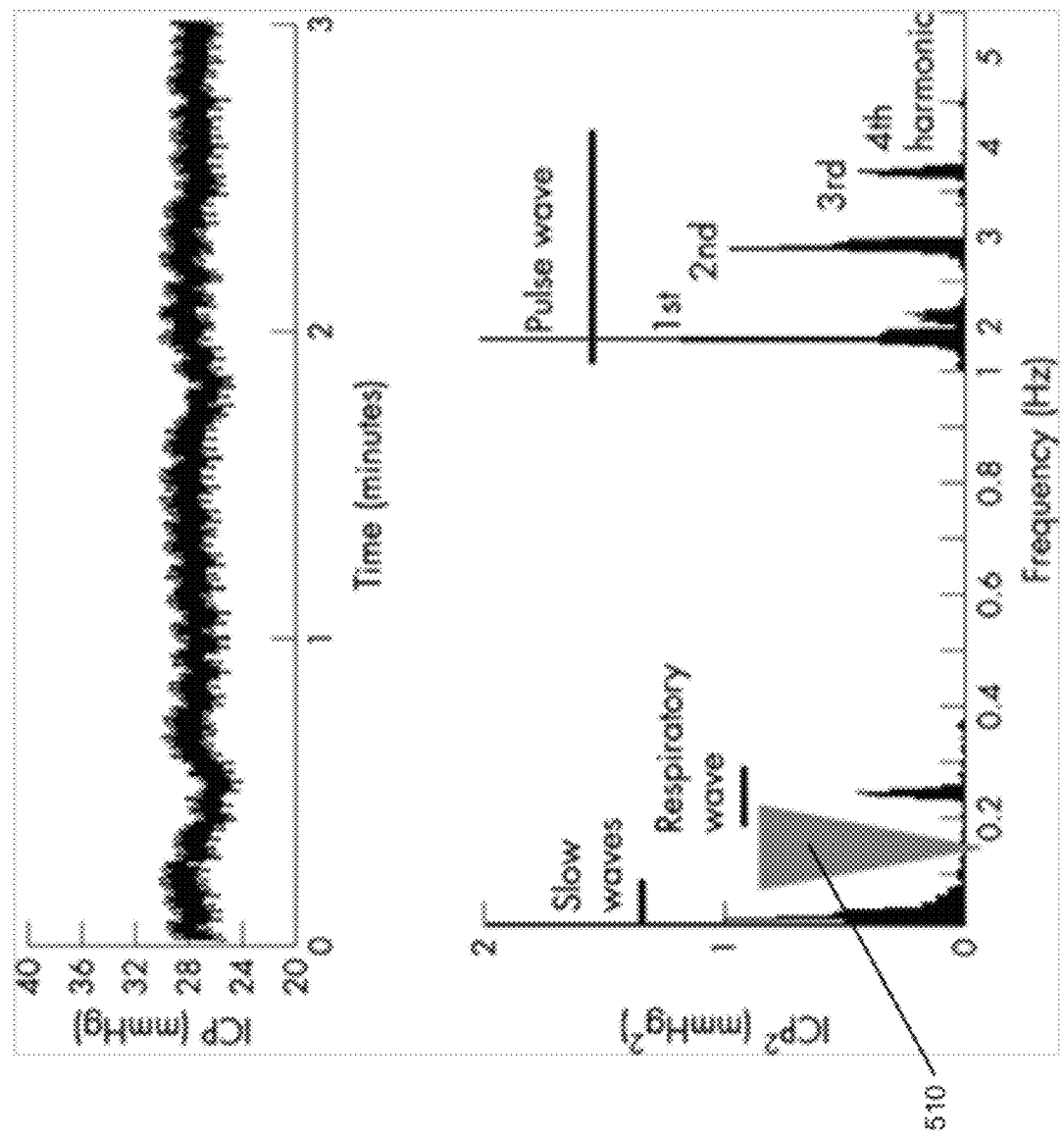

FIG. 5 (in the upper graph) shows the Fourier transform of intracranial pressure (ICP) showing the normal wave components. Referring to FIG. 5, three prominent wave components are shown: 1) the pulse frequency, 2) the respiratory frequency, and 3) the so-called slow wave frequency. Pulse and respiratory waves are faster (i.e., have a higher frequency) than autoregulatory responses, so they are always transmitted passively and are generally not useful for autoregulation analysis. Slow waves shown at a frequency of about 0.05 hertz (Hz) are slower than the autoregulatory response, so they are either blunted or phased shifted in intracranial measurements when compared with systemic blood pressure measurements.

In accordance with one implementation consistent with the invention, the ideal theoretical wave for autoregulation analysis has been determined to be the fastest wave that is still slower than the autoregulatory response, and lies in the transitional band between respiratory and slow waves, shown via the triangle labeled 510 in the lower graph in FIG. 5. For example, the bandwidth may range from about 0.05 Hz to about 0.2 Hz.

Figure 6:
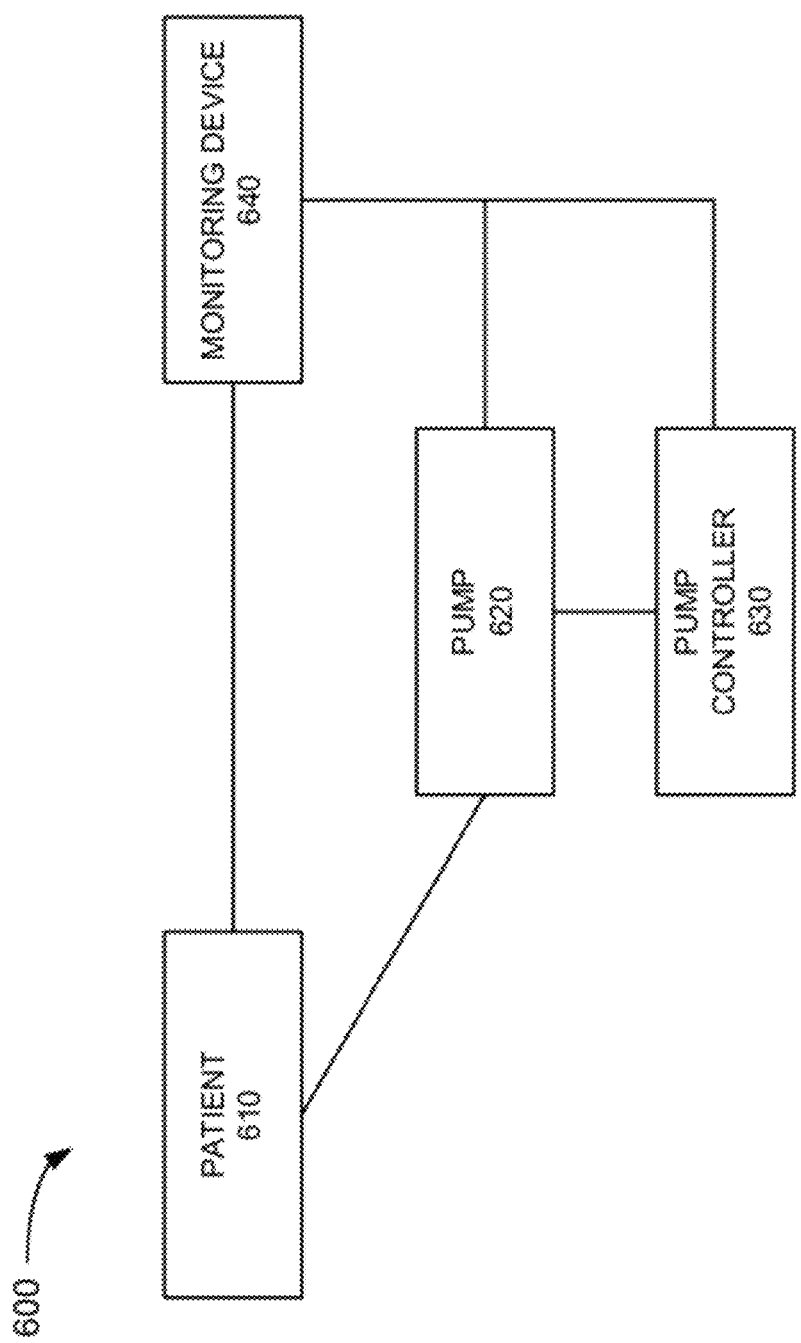
FIG. 6 illustrates an exemplary environment in which systems and methods described herein may be implemented.

As described above, CPB may be used to introduce slow waves into the patient that will be used to identify whether the patient's autoregulatory mechanism is working properly. For example, FIG. 6 is a block diagram of an exemplary environment in which systems and methods described herein may be implemented. Referring to FIG. 6, environment 600 may include a patient 610, a pump 620, a pump controller 630 and a monitoring device 640.

Patient 610 may represent any person (i.e., an adult or child) that may be in a state of medical distress or has sustained an injury. Pump 620 may include a pump and associated equipment used during CPB to provide or augment blood flow to patient 610. Pump controller 630 may include components used to control pump 620. In an exemplary implementation, pump controller 630 may vary or oscillate the flow rate of pump 620 to create slow waves in patient 610, as described in more detail below.

Monitoring device 640 may include a device used to continuously monitor various parameters associated with patient 610. In an exemplary implementation, monitoring device 640 may receive data from patient 610 and/or equipment connected to patient 610 to define an autoregulatory range for patient 610, as described below. This information may then be used to regulate blood flow from pump 620 to provide the proper blood flow to patient 610 to allow the patient's 610 brain to autoregulate properly, as described in detail below.

Exemplary environment 600 illustrated in FIG. 6 is provided for simplicity. It should be understood that a typical environment may include more or fewer devices than illustrated in FIG. 6. For example, pump controller 630 is shown as a separate element from pump 620. In other implementations, pump controller 630 may be part of or integral with pump 620. In addition, in some implementations, the functions described below as being performed by multiple devices in environment 600 may be performed by a single device. For example, in some implementations, the functions performed by pump controller 630 and monitoring device 640 may be combined into a single device. In addition, in an alternative implementation, some elements may not be used.

Figure 7:
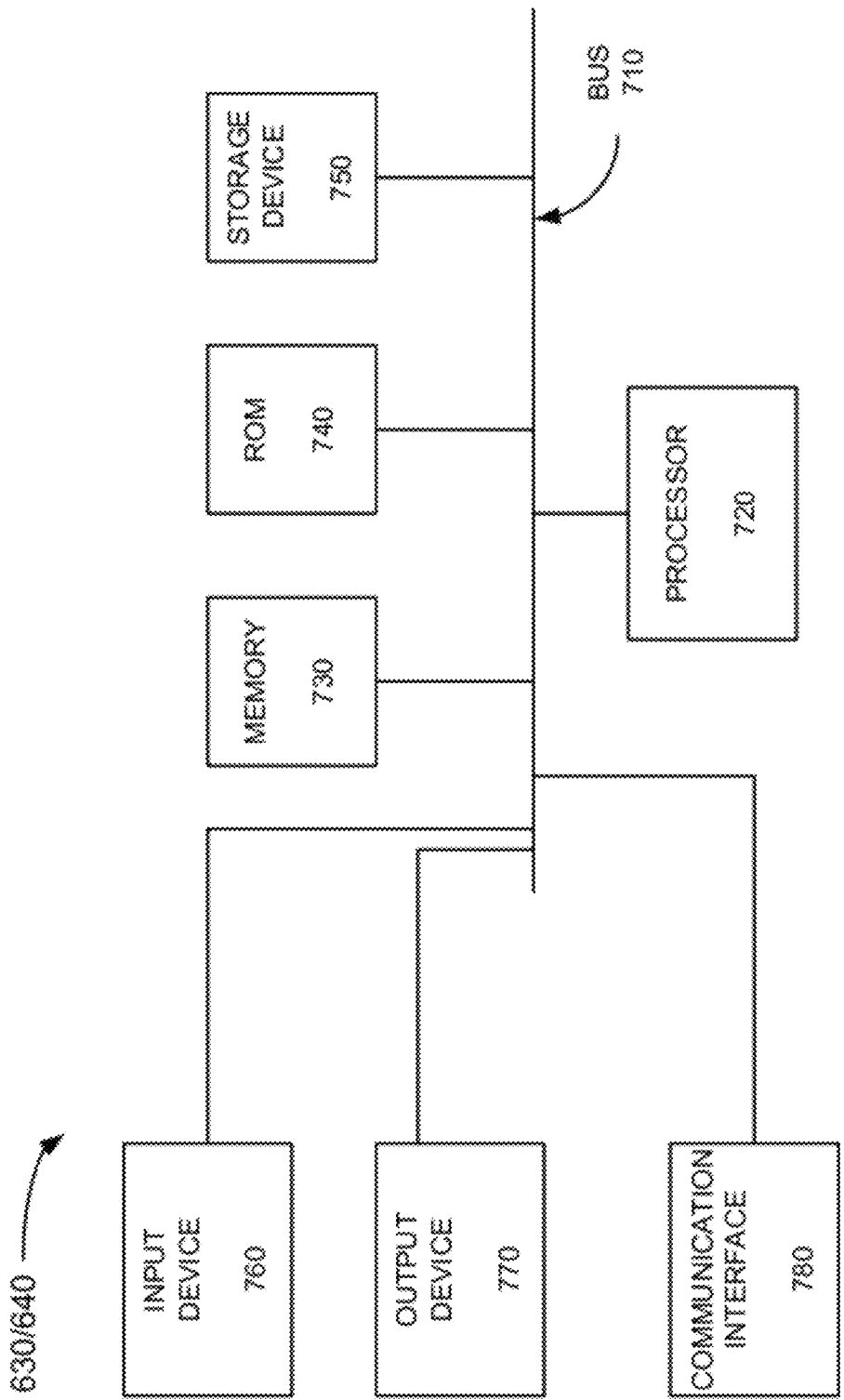
FIG. 7 illustrates an exemplary configuration of one or more of the devices of FIG. 6.

FIG. 7 illustrates an exemplary configuration of pump controller 630. Monitoring device 640 may be configured in a similar manner. Referring to FIG. 7, pump controller 630 may include bus 710, processor 720, main memory 730, read only memory (ROM) 740, storage device 750, input device 760, output device 770, and communication interface 780. Bus 710 may include a path that permits communication among the elements of pump controller 630.

Processor 720 may include a processor, microprocessor, application specific integrated circuit (ASIC), field programmable gate array (FPGA) or processing logic that may interpret and execute instructions. Memory 730 may include a random access memory (RAM) or another type of dynamic storage device that may store information and instructions for execution by processor 720. ROM 740 may include a ROM device or another type of static storage device that may store static information and instructions for use by processor 720. Storage device 750 may include a magnetic and/or optical recording medium and its corresponding drive.

Input device 760 may include a mechanism that permits an operator to input information to pump controller 630, such as a keyboard, control keys, a mouse, a pen, voice recognition and/or biometric mechanisms, etc. Input device 760 may also include one or more control buttons, knobs or keypads to allow an operator to set various parameters with respect to controlling environment 600.

Output device 770 may include a mechanism that outputs information to the operator, including a display, a printer, a speaker, etc. For example, output device 770 may include a display screen (e.g., a liquid crystal display (LCD) or another type of display) that provides information to a health care provider regarding patient 610.

Communication interface 780 may include a transceiver that enables pump controller 630 to communicate with other devices and/or systems. For example, communication interface 780 may communicate with pump 620 and monitoring device 640. Communication interface 780 may also include a modem or an Ethernet interface to a local area network (LAN). Alternatively, communication interface 780 may include other mechanisms for communicating via a network (not shown).

Pump controller 630 may perform processing associated with providing slow wave inputs to pump 620/patient 610, as described above. According to an exemplary implementation, pump controller 630 may perform these operations in response to processor 720 executing sequences of instructions contained in a computer-readable medium, such as memory 730. A computer-readable medium may be defined as a physical or logical memory device.

The software instructions may be read into memory 730 from another computer-readable medium, such as data storage device 750, or from another device via communication interface 780. The software instructions contained in memory 730 may cause processor 720 to perform processes that will be described later. Alternatively, hard-wired circuitry may be used in place of or in combination with software instructions to implement processes described herein. Thus, implementations described herein are not limited to any specific combination of hardware circuitry and software.

Figure 8:
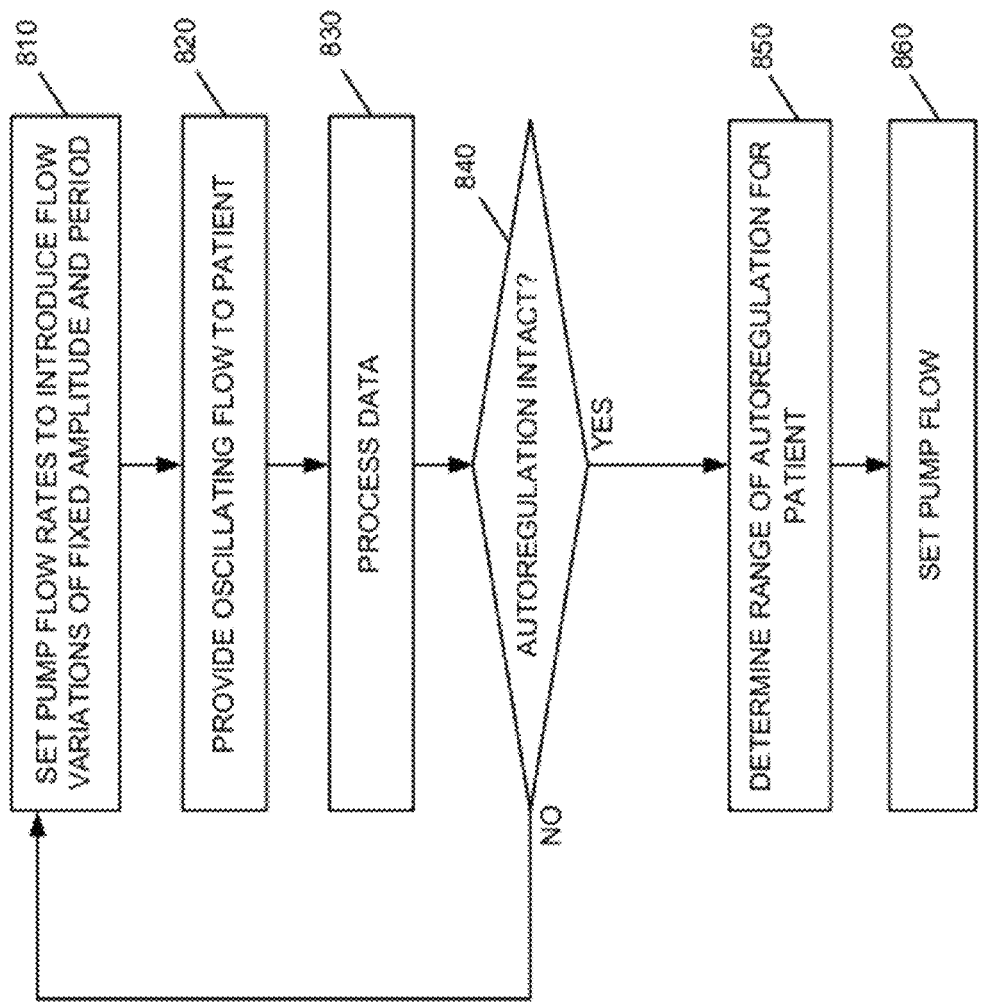
FIG. 8 is a flow diagram illustrating exemplary processing by various devices illustrated in FIG. 6.

FIG. 8 is a flow diagram illustrating exemplary processing associated with inducing or inputting slow waves to patient 610 via pump 620. In this example, assume that patient 610 is on CPB and pump 620 is providing all or some of the blood flow to patient 610. Processing may begin with a health care provider setting pump controller 630 to introduce flow variations to patient 610 that have a fixed amplitude and period (block 810). For example, in one implementation, the flow rates may be selected to provide an input that oscillates the output of pump 620 to generate consistent, repeatable blood sinusoidal flow waves in patient 610.

As one example, pump controller 630 may be set to vary the output of pump 620 between two flow rates calibrated in, for example, liters/minute or cubic centimeters (cc)/minute, to create an oscillating input varying from one flow rate to another flow rate. This varying/oscillating input may create a slow wave in patient 610's brain. In one implementation, the induced slow wave may have a frequency ranging from about 0.05 Hz to 0.2 Hz. For example, pump controller 630 may be set to oscillate or vary the input from one flow rate to another flow rate at a relatively slow rate (e.g., every 20 seconds), such as a flow rate ranging from 145 cubic centimeters (cc) per kilogram (kg) weight of patient 610 per minute (min) to 150 cc/kg/min. Varying the output of pump 620 every 20 seconds in this manner may generate corresponding slow waves in patient 610's brain having a frequency of 0.05 Hz.

In some implementations, pump controller 630 may be set to allow medical personnel to vary the output of pump 620 to produce slow waves having a desired frequency directly (e.g., without having to set particular varying flow rates) to generate slow waves in patient 610's brain having the desired frequency. For example, pump controller 630 may allow medical personnel to set the flow rate from pump 620 to create an oscillating input varying between 145 and 150 cc/kg/min every 30 seconds. In this case, the frequency of the corresponding slow wave may then be approximately 0.03 Hz.

In each case, pump 620 may then provide blood to patient 610 at the desired oscillation amplitude and frequency (block 820). That is, in this example, pump 620 may output blood flow that varies in a sinusoidal manner to create the input waveform in patient 610's brain. In other instances, pump controller 630 may control pump 620 to vary the blood flow in a non-sinusoidal manner (e.g., to provide parametrically or programmatically shaped input waves). In each case, monitoring device 640 may then monitor and process various parameters in patient 610 at the input wave frequency to determine whether patient 610's brain is responding to the fixed oscillations (block 830).

For example, monitoring device 640 may monitor the blood volume in patient 610's brain in the frequency domain at the frequency of the input wave (e.g., 0.05 Hz in this example) to determine whether the blood volume is going up or down with the oscillating output of pump 620, or whether the blood volume is phase shifted with respect to the oscillating output from pump 620. In some instances, when autoregulation is intact in patient 610, the peak volume of blood (or intracranial pressure (ICP), cerebral blood flow, or cerebral oxygen content) in patient 610's brain may be phase shifted with respect to the peak volume of blood flow provided by pump 620. For example, the blood volume (or ICP, cerebral blood flow, or cerebral oxygen content) in the brain of patient 610 may be phase shifted (e.g., the peak occurs earlier or later) by an amount ranging from, for example, 90-180° (or more) with respect to the blood flow output by pump 620 when the brain's autoregulatory mechanism is intact. In one implementation, the blood volume in the brain of patient 610 has been shown to be phase shifted 180° from the arterial blood pressure (ABP) or blood flow input wave during intact autoregulation, and 0° phase shifted from the ABP or blood flow input wave during impaired autoregulation.

The blood flow parameters from pump 620 and the information gathered by monitoring device 640 may then be analyzed to determine whether autoregulation of patient 610's brain is intact (block 840) and/or identify the proper settings for pump 620 such that patient 610's autoregulatory mechanism will function properly. For example, monitoring device 640 may receive information from pump controller 630 indicating the input wave frequency. Monitoring device 640 may then analyze the volume of blood in patient 610's brain at the input wave frequency. If the frequency analysis indicates that the blood volume in patient 610's brain is 0° phase shifted from the input blood volume wave provided by pump 620, monitoring device 640 may determine that autoregulation of patient 610's brain may not be working (block 840—no). That is, the volume of blood in patient 610's brain is merely going up and down in correlation to the blood volume being provided by pump 620.

In this case, processing may return to block 810. For example, pump controller 630 and/or personnel associated with monitoring patient 610 may reset the blood flow from pump 620 to provide blood flow at a lower (or higher) ABP and to generate an input wave in patient 610's brain to determine the appropriate setting or range of settings in which autoregulation is functioning properly (block 810). That is, pump controller 630 may be set to provide an oscillating ABP input wave (e.g., a sinusoidal input wave or other input wave having a particular input frequency) in patient 610's brain at a lower blood pressure (or higher blood pressure) that can be analyzed as described above to determine if autoregulation in patient 610's brain is operating properly at the new blood pressure being provided to patient 610.

Referring back to block 840, if monitoring device 640 determines that peak blood volume (or ICP, cerebral blood flow, or cerebral oxygen content) in the brain of patient 610 is phase shifted (e.g., negative phase shifted where the peak occurs earlier) by an amount ranging from, for example, 100° to 180° (or more) with respect to the blood flow output by pump 620, monitoring device 640 may determine that the brain's autoregulatory mechanism is intact (block 840—yes).

In some implementations, monitoring device 640 and/or personnel associated with caring for patient 610 may determine a range of autoregulation for patient 610 (block 850). For example, monitoring device 640 may use the blood pressure when autoregulation has been found to be intact as part of a range of blood pressures and attempt to identify a higher value and/or lower value in which the autoregulatory mechanism remains intact. As an example, monitoring device 640 and/or medical personnel associated with monitoring patient 610 may provide varying flow rates to produce input waves having a higher and lower blood pressure than the blood pressure identified in which autoregulation is operating properly, to attempt to identify the higher and lower ranges in which autoregulation is functioning properly.

After the range of flow rates/blood volume have been identified, this information may be used to set the flow rate and/or pressure of pump 620 (block 860). That is, the flow rate of pump 620 is set to provide a flow and/or pressure of blood such that the autoregulatory mechanism of patient 610's brain is functioning properly. In some implementations, monitoring device 640 may communicate with pump controller 630 to automatically set the flow rate and/or pressure to a range in which the autoregulatory mechanism of patient 610's brain is functioning properly. Human personnel may also monitor the settings associated with pump 620 via output device 770 (e.g., an LCD screen). In this manner, medical personnel may quickly ascertain certain conditions and optimize care for a patient on CPB.

Figure 9:
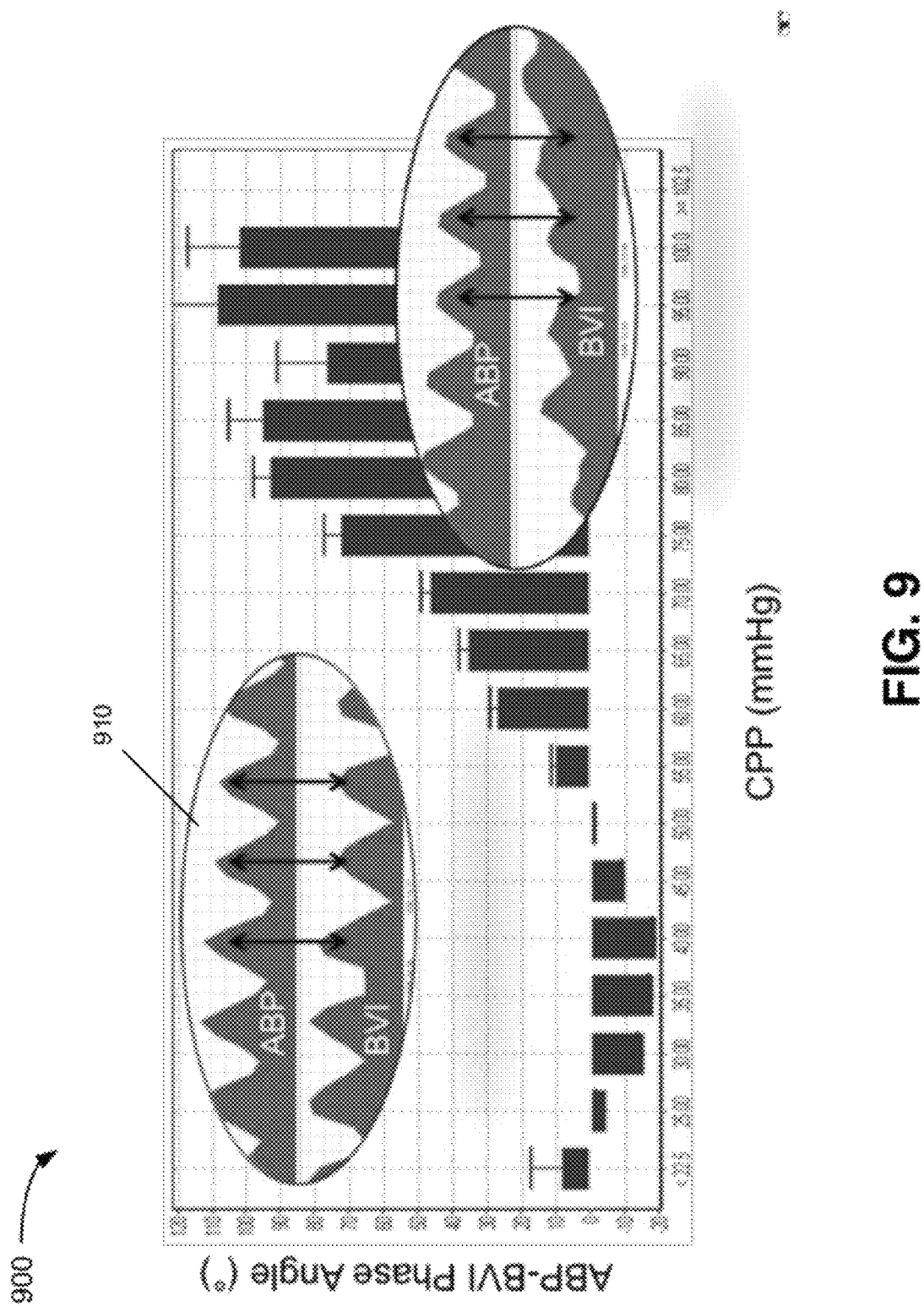
FIG. 9 illustrates an exemplary output graph generated by one of the devices of FIG. 6 in accordance with an exemplary implementation.

FIG. 9 illustrates an exemplary output 900 generated by monitoring device 640 for a piglet on bypass. As illustrated in FIG. 9, the y axis of graph 900 measures the phase angle difference between the arterial blood pressure (ABP) waveform provided by pump 620 and the blood volume index (BVI), which corresponds to the blood volume in the brain. In this case, as illustrated by insert 910, at a cerebral perfusion pressure (CPP) of about 50 mm Hg or less, the peak BVI is depicted as lagging or negative phase shifted with respect to the peak ABP. In this example, however, the BVI is not corrected for a delay associated with the monitoring device used in this example. In this experiment, when the delay is corrected for, it was found that the peak BVI is approximately 180° phase shifted with respect to the peak ABP when the piglet's autoregulation is intact, and when the BVI waveform is 0° phase shifted from the ABP input wave form (i.e., the BVI is in phase with the ABP), the piglet's autoregulation is impaired. Therefore, in this example, it was found that a CPP of greater than 55 mm of Hg resulted in intact autoregulation for the piglet.

Monitoring device 640 may output similar graphs for patient 610 on bypass. That is, monitoring device 640 may output graphs displaying blood volume/ABP phase angle differences versus CPP. As discussed above, when the measured blood volume (e.g., BVI) in patient 610's brain is phase shifted, such as negative phase shifted (or positive phase shifted) by an amount greater than 100°, from the peak blood volume or pressure provided by pump 620, this may indicate a setting at which patient 610's autoregulation mechanism is intact. Medical personnel may then determine a range of autoregulation, including a LLA, to allow the medical personnel to set pump 620 to provide the desired flow rate of blood and/or blood pressure to patient 610.

In addition, the time required for medical personnel to identify the proper flow rate using the methodology described above may be significantly reduced as compared to other methodologies. For example, the time needed to identify the autoregulation range according the methodology described above may be as low as a few minutes or less, as compared to 30 minutes or more for other methodologies. Further, since the induced slow waves described above are repetitive and uniform in amplitude, the accuracy and precision associated with measuring a range of autoregulation for a patient is greater than that obtained via other methodologies.

CONCLUSION

Implementations described herein provide repetitive, hemodynamic oscillations in a patient via a bypass pump 620. The flow variations may generate a corresponding slow wave in patient 610's brain that may be monitored to identify a flow rate at which autoregulation of patient 610's brain is functioning properly. Advantageously, by introducing fixed wave inputs having a known frequency, more precise and accurate measurements with respect to identifying a flow rate associated with proper autoregulation may be made. Further, the time required for identifying the proper flow rate may be significantly reduced as compared to other methodologies.

The foregoing description of exemplary implementations provides illustration and description, but is not intended to be exhaustive or to limit the invention to the precise form disclosed. Modifications and variations are possible in light of the above teachings or may be acquired from practice of the invention.

For example, various features have been described above with respect to various devices performing various functions. In other implementations, the functions described as being performed by a particular device may be performed by another device. In addition, functions described as being performed by a single device may be performed by multiple devices, or vice versa.

It will be apparent to one of ordinary skill in the art that various features described above may be implemented in many different forms of software, firmware, and hardware in the implementations illustrated in the figures. The actual software code or specialized control hardware used to implement the various features is not limiting of the invention. Thus, the operation and behavior of the features of the invention were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as a processor, a microprocessor, an application specific integrated circuit, or a field programmable gate array, software, or a combination of hardware and software.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A method, comprising:
    setting a cardiopulmonary bypass pump to alternate output of the cardiopulmonary bypass pump between a first flow rate and a second flow rate to induce generation of a slow wave in a brain of a patient via blood flow variations provided to the patient by the alternating output of the cardiopulmonary bypass pump;
    analyzing, via a monitoring device, a response waveform via blood volume in the brain of the patient with respect to the slow wave; and
    determining, by the monitoring device and based on the analyzing, whether an autoregulatory mechanism associated with the brain is operating properly.

2. The method of claim 1, wherein the analyzing is performed in a frequency domain.

3. The method of claim 2, wherein the determining comprises:
    determining whether peak blood volume in the brain, measured at a frequency corresponding to an input frequency of the blood flow variations, is phase shifted with respect to the peak blood volume provided by the cardiopulmonary bypass pump.

4. The method of claim 1, further comprising:
    setting a third flow rate of the cardiopulmonary bypass pump based on determining that the autoregulatory mechanism is operating properly.

5. The method of claim 1, wherein the alternating output of the cardiopulmonary bypass pump introduces blood flow variations that are of fixed amplitude and duration and induce the generation of the slow wave corresponding to a sinusoidally varying slow wave.

6. The method of claim 5, wherein a frequency of input associated with the blood flow variations is set to a value ranging from 0.05 hertz (Hz) to about 0.2 Hz.

7. The method of claim 1, wherein the alternating output of the cardiopulmonary bypass pump introduces blood flow variations that induce the generation of the slow wave corresponding to a parametrically varying slow wave.

8. A system, comprising:
    a pump controller configured to set flow rates of a cardiopulmonary bypass pump to vary output of the cardiopulmonary bypass pump between a first flow rate and a second flow rate to introduce blood flow variations to a patient corresponding to an input wave having a first frequency; and at least one monitoring device configured to:
analyze blood volume in a brain of the patient with respect to the blood flow variations, and
determine, based on the analyzed blood volume, whether an autoregulatory mechanism associated with the brain is operating properly.

9. The system of claim 8, wherein the at least one monitoring device is further configured to:
determine whether peak blood volume in the brain, measured at the first frequency, is phase shifted with respect to peak blood flow or pressure provided by the cardiopulmonary bypass pump, and
determine that the autoregulatory mechanism is working properly, in response to determining that peak blood volume, measured at the first frequency, is phase shifted with respect to the peak blood flow or pressure provided by the cardiopulmonary bypass pump.

10. The system of claim 8, wherein the pump controller is further configured to:
set a third flow rate of the cardiopulmonary bypass pump based on information provided by the at least one monitoring device indicating that the autoregulatory mechanism is operating properly.

11. The system of claim 8, wherein the pump controller is configured to:
automatically set a third flow rate or pressure of the cardiopulmonary bypass pump based on information provided by the at least one monitoring device.

12. The system of claim 8, wherein the first frequency is set to a value ranging from 0.05 hertz (Hz) to about 0.2 Hz.

13. The system of claim 8, wherein the pump controller is configured to introduce blood flow variations having a fixed amplitude and duration to generate a sinusoidal input wave.

14. The system of claim 8, wherein the pump controller is configured to introduce blood flow variations corresponding to a parametric waveform.

15. A non-transitory computer-readable medium having stored thereon sequences of instructions which, when executed by at least one processor, cause the at least one processor to:
set flow rates of a cardiopulmonary bypass pump to vary output of the cardiopulmonary bypass pump between a first flow rate and a second flow rate to introduce blood flow variations to a patient;
analyze blood volume in a brain of the patient with respect to the blood flow variations; and
determine whether an autoregulatory mechanism associated with the brain is functioning properly based on the analyzing.

16. The non-transitory computer-readable medium of claim 15, wherein when determining whether an autoregulatory mechanism associated with the brain is functioning properly, the instructions cause the at least one processor to:
determine whether peak blood volume in the brain, measured at a first frequency, is negative phase shifted with respect to peak blood flow rate or pressure provided by the cardiopulmonary bypass pump, and
determine that the autoregulatory mechanism is working properly, in response to determining that the peak blood volume, measured at the first frequency, is negative phase shifted with respect to the peak blood flow rate or pressure provided by the cardiopulmonary bypass pump.

17. The non-transitory computer-readable medium of claim 15, further including instructions for causing the at least one processor to:
automatically adjust the cardiopulmonary bypass pump to provide a first third flow rate or pressure in which the autoregulatory mechanism is working properly.

18. The non-transitory computer-readable medium of claim 15, wherein when setting the flow rates of the cardiopulmonary bypass pump, the instructions cause the at least one processor to:
introduce blood flow variations to produce an input wave in the patient's brain.

19. The non-transitory computer-readable medium of claim 18, wherein when setting the flow rates of the cardiopulmonary bypass pump, the instructions cause the at least one processor to generate the input wave having a frequency ranging from 0.05 hertz (Hz) to about 0.2 Hz.

20. The non-transitory computer-readable medium of claim 18, wherein when analyzing the blood volume in the brain, the instructions cause the at least one processor to:
analyze the blood volume at a frequency corresponding to the frequency of the input wave.

* * * * *

UNITED STATES PATENT AND TRADEMARK OFFICE
CERTIFICATE OF CORRECTION

PATENT NO. : 9,474,451 B2  
APPLICATION NO. : 13/433348  
DATED : October 25, 2016  
INVENTOR(S) : Ken M. Brady et al.

Page 1 of 1

It is certified that error appears in the above-identified patent and that said Letters Patent is hereby corrected as shown below:

In the Claims

Claim 17, at Column 12, Line 26 change the phrase "a first third flow rate or pressure" to "a third flow rate or pressure".

Signed and Sealed this  
Ninth Day of May, 2017

Michelle K. Lee  
*Director of the United States Patent and Trademark Office*